US006451295B1

(12) United States Patent
Cai et al.

(10) Patent No.: US 6,451,295 B1
(45) Date of Patent: Sep. 17, 2002

(54) CLEAR ANTIPERSPIRANTS AND DEODORANTS MADE WITH SILOXANE-BASED POLYAMIDES

(75) Inventors: Heng Cai, Yardley, PA (US); Adriana Urrutia-Gutierrez, Mexico City (MX); Aixing Fan, Bridgewater, NJ (US)

(73) Assignees: Colgate-Palmolive Company, New York, NY (US); Dow-Corning Corporation, Midland, MI (US)

( * ) Notice: Subject to any disclaimer, the term of this patent is extended or adjusted under 35 U.S.C. 154(b) by 0 days.

(21) Appl. No.: 09/922,054

(22) Filed: Aug. 3, 2001

Related U.S. Application Data

(63) Continuation-in-part of application No. 09/873,504, filed on Jun. 4, 2001.
(60) Provisional application No. 60/229,445, filed on Aug. 31, 2000.

(51) Int. Cl.[7] .......................... A61K 7/32; A61K 31/74; A61K 7/00
(52) U.S. Cl. .................. 424/65; 424/78.02; 424/78.08; 424/400; 424/401
(58) Field of Search ................................ 424/65, 78.02, 424/78.08, 400, 401

(56) References Cited

U.S. PATENT DOCUMENTS

| | | | |
|---|---|---|---|
| 3,441,537 A | 4/1969 | Lengnick | |
| 4,322,400 A | 3/1982 | Yuhas | |
| 4,673,570 A | 6/1987 | Soldati | |
| 4,853,214 A | 8/1989 | Orr | |
| 4,937,069 A | 6/1990 | Shin | |
| 5,019,375 A | 5/1991 | Tanner et al. | |
| 5,069,897 A | 12/1991 | Orr | |
| 5,102,656 A | 4/1992 | Kasat | |
| 5,120,521 A | 6/1992 | Wells et al. | |
| 5,243,010 A | 9/1993 | Choi et al. | |
| 5,272,241 A | 12/1993 | Lucarelli et al. | |
| 5,302,382 A | 4/1994 | Kasprzak | |
| 5,603,925 A | 2/1997 | Ross et al. | |
| 5,871,720 A | 2/1999 | Gutierrez et al. | |
| 5,919,441 A | 7/1999 | Mendolia et al. | |
| 5,981,680 A | 11/1999 | Petroff et al. | |
| 6,051,216 A | * 4/2000 | Barr et al. ..................... 424/65 |

FOREIGN PATENT DOCUMENTS

| | | |
|---|---|---|
| EP | 291 334 | 5/1988 |
| WO | WO 92/05767 | 10/1990 |
| WO | WO 99/06473 | 8/1997 |

OTHER PUBLICATIONS

J. Liquid Chromatography, vol. 9, pp. 783–804, 1986.
*An Introduction to the Mechanics of Solids*, (Edited by Lardner, T.J.; McGraw–Hill, 1978)*Note–This book is out of print and we are trying to obtain a copy. A copy of the material will be forwarded to the U.S.P.T.O. when available or a substitute document will be sent based on company records.
Chemistry and Technology of Silicones (Academic Press, Inc.) Orlando, FL, 1968; pp. 190–196 and 239–245.

\* cited by examiner

*Primary Examiner*—Shelley A. Dodson
(74) *Attorney, Agent, or Firm*—Rosemary M. Miano; James DeCesare

(57) ABSTRACT

Clear antiperspirant and/or deodorant compositions, especially clear sticks having good structural integrity, can be formed by incorporating at least 8% by weight based on the total weight of the composition of a selected siliconized polyamide into a product formulated with at least one silicone material and at least one non-silicone emollient. The siliconized polyamides have the silicone portion in the acid side of the polyamide and are selected so that: (a) the degree of polymerization in the silicone portion is in the range of 12-18; (b) the average molecular weight of the siliconized polyamide is at least 50,000 daltons with at least 95% of the polyamide having a molecular weight greater than 10,000 as measured by size exclusion chromatography; and (c) the polydispersity is less than 20.

22 Claims, No Drawings

CLEAR ANTIPERSPIRANTS AND DEODORANTS MADE WITH SILOXANE-BASED POLYAMIDES

This invention is a continuation-in-part under 35 USC Section 120 based on U.S. patent application Ser. No. 09/873,504, filed on Jun. 4, 2001, which in turn claims priority under 35 USC 119(e)(1) based on Provisional application Serial No. 60/229,445, filed Aug. 31, 2000.

FIELD OF THE INVENTION

The use of polyamides in cosmetic compositions, especially antiperspirants and/or deodorants, has certain advantages, especially with regard to clarity. It has been difficult, however, to obtain satisfactory structural integrity for prolonged periods of time with such compounds. By the use of selected types of polyamides, products of this invention are obtained which provide clear products with improved structural stability and integrity.

BACKGROUND OF THE INVENTION

The present invention is directed to improved cosmetic compositions formed with a specific group of polyamide gelling agents previously described in (1) U.S. Pat. No. 6,051,216 (WO 99/06473); (2) U.S. Provisional patent application No. 60/229,444, filed on Aug. 31, 2000; and (3) a second application based on (2) as a continuation-in-part case, referenced as as Ser. No. 09/922,091 and which is being filed on the same date as this patent application, all of which are incorporated by reference herein in their entirety.

While a number of references have disclosed polyamides as a class of compounds, it has been found that certain polyamides containing siloxane portions in the acid component may be used to form cosmetic compositions with enhanced structural properties.

Cosmetic compositions (for example, a solid cosmetic composition, such as a gel, soft-solid or semi-solid (cream), or stick), may be made with a base composition containing at least one silicone fluid (for example, silicone liquids such as silicone oils) which is thickened using a siliconized polyamide as a gelling agent; a carrier in which cosmetically active materials are incorporated; and at least one active ingredient to provide the activity for such cosmetic composition. Particular embodiments of the present invention include deodorant and antiperspirant compositions (and base compositions therefor), in which the cosmetically active ingredient is a deodorant active material and/or an antiperspirant active material. Embodiments of the present invention are not limited, however, to such antiperspirant and/or deodorant compositions, and are also directed to other cosmetic compositions containing other cosmetically active ingredients, such as sun protection compositions containing sun-screen agents as the active material.

Preferred embodiments of formulated cosmetic products are directed to cosmetic compositions which are transparent (clear), including solid transparent (clear) compositions, especially transparent (clear) deodorant and/or antiperspirant compositions which are sticks or gels. While selected embodiments of cosmetic compositions made with the polyamides described are preferably clear or transparent, the cosmetic compositions need not, however, be clear or transparent, and can be translucent, or opaque.

The selected siloxane-based polyamides and mixtures thereof are used as gelling agents in cosmetic products, especially antiperspirants and/or deodorants. The compositions made with the siloxane-based polyamides have improved application and cosmetic properties (including reduced tackiness and stickiness), and, more preferably, have improved clarity and low to no white residue properties. They also exhibit improved stick integrity as compared to earlier efforts with such compositions.

Antiperspirant products are well known in the art. Antiperspirant products have appeared in the marketplace in various dosage forms, such as sticks, gels, roll-ons, aerosols and creams. Generally, these dosage forms include a solution of the active ingredient in a solvent, a suspension of the active ingredient in a non-solvent, or a multi-phase dispersion or emulsion in which a solution of the active ingredient is dispersed in some continuous phase or in which the solubilized active ingredient constitutes a continuous phase.

Of the above-referred-to dosage forms, the roll-on is an example of a liquid form composition, the stick form is an example of a solid form composition, and the gel form is structured liquid which may or may not be a solid (for example, under some circumstances gels can flow). The stick form can be distinguished from a gel on the basis that in a stick the formulated product can maintain its shape for extended time periods outside the package (allowing for some shrinkage due to solvent evaporation), while a gel cannot so maintain its shape. Adjustment of amounts of gelling or thickening agents such as bentones, fumed silica, polyethylene, stearyl alcohol or castor wax, can be used in order to form a gel or stick.

Gels, pastes and creams (which are also known as soft-solids or semi-solids) can be suitably packaged in containers which have the appearance of a stick, but which dispense through apertures (for example, slots or pores) on the top surface of the package. These products have been called soft sticks or "smooth-ons". These products hereinafter are generically called "gels". Reference is made to U.S. Pat. No. 5,102,656 to Kasat, U.S. Pat. No. 5,069,897 to Orr, and U.S. Pat. No. 4,937,069 to Shin, each of which discloses such gels, including physical characteristics thereof such as viscosity and hardness. The contents of each of these three U.S. Patents are incorporated herein by reference in their entirety.

A representative composition which can be dispensed through apertures is described in U.S. Pat. No. 5,102,656 to Kasat. This disclosed composition is a creamy, heterogeneous anhydrous antiperspirant product containing, in percent by weight, of the total weight of the composition, 30%–70% of a volatile silicone as a carrier, 7–30% of a suitable gelling agent or agents, and about 12–30% of a physiologically acceptable antiperspirant agent. This patent discloses that the gelling agent can be any of a number of materials, including, for example, hydrogenated vegetable oil, hydrogenated castor oil, fatty acids having from 14 to 36 carbon atoms, beeswax, paraffin wax, fatty alcohols having from 14 to 24 carbon atoms, polyethylene and the like.

Clear or translucent antiperspirant gels (which have been dispensed from containers having the appearance of a stick) have been marketed, consisting of viscous, high internal phase emulsions. These gels exhibit some advantages but these emulsions also suffer from various disadvantages, including often requiring the use of ethanol to achieve desired aesthetics. In connection with these emulsions, see U.S. Pat. No. 4,673,570 to Soldati and PCT (International Application) Publication No. WO 92/05767.

U.S. Pat. No. 5,120,531 to Wells, et al discloses rinse-off hair conditioner and styling compositions providing a gel-network thickened vehicle for the styling polymer and solvent. This patent discloses various siloxanes as the conditioning agent including polydiorganosiloxanes having quaternary ammonium-substituted groups attached to the silicon, and polydiorganosiloxanes having silicone-bonded substituents which are amino-substituted hydrocarbon groups.

U.S. Pat. No. 5,500,209 discloses a gel or stick which includes active deodorant and/or antiperspirant ingredients, a polyamide gelling agent, and a solvent for the polyamide gelling agent, in which the gel or stick composition can be clear or translucent. This patent discloses that the polyamide gelling agent is soluble in a cosmetically acceptable solvent at elevated temperatures, and solidifies (gels) upon cooling; acceptable solvents are disclosed as including various alcohols, including various glycols. While the polyamide-containing stick or gel disclosed in the aforementioned patent contains desirable properties in connection with stability of the composition, (particularly in the presence of acidic antiperspirant active materials, and in providing clear or translucent gel or stick compositions) such formulas may result in tackiness and stickiness both upon and after application to the skin.

Addressing this problem of tackiness and stickiness in connection with cosmetic compositions utilizing a polyamide gelling agent, U.S. patent application Ser. No. 08/426,672, now U.S. Pat. No. 5,603,925, the contents of which are incorporated herein by reference in their entirety, discloses the use of a specific solvent system for a solid composition containing an antiperspirant active material and a polyamide gelling agent. This solvent system is glycol-free and contains a non-ionic surfactant and a polar solvent. Water is the polar solvent, and the non-ionic surfactant acts as a dispersing medium for the antiperspirant active material, in which sufficient water is used to give a clear or translucent solution/emulsion of the antiperspirant active material.

A typical technique to reduce the tackiness of, for example, antiperspirant formulations is the incorporation of one or more cyclomethicones (tetra- penta- or hexa-cyclodimethyl-siloxanes or mixtures thereof). These cyclomethicones are very low-viscosity silicone liquids that provide excellent lubricity but do not leave stains on the skin and/or clothing. More than 50% by weight of cyclomethicone has been incorporated into solid stick antiperspirant formulations, for example, using a wax solidifying agent. However, cyclomethicone is a nonsolvent for the dimer based polyamides described as gelling agents in U.S. Pat. No. 5,500,209. Moreover, only limited quantities of the cyclomethicone can be incorporated in solid compositions gelled using such polyamide gelling agent, without destroying the clarity of the gelled composition. Beyond that point, the gelled composition becomes cloudy because of either excessive crystallization of the polyamide or immiscibility of the cyclomethicone in the mixture.

U.S. Pat. No. 5,243,010 to Choi, et al., discloses aromatic polyamide resins having pendant silyl groups.

U.S. Pat. No. 5,272,241 to Lucarelli, et al., discloses organofunctional siloxanes useful in both the personal care and plastics industries, the siloxanes being amino acid functionalized silicones.

U.S. patent application Ser. No. 08/790,351, now U.S. Pat. No. 5,919,441, assigned to The Mennen Company describes in general the use of polyamides as gelling agents for cosmetic compositions.

Other gellant systems that may be used include those made with an n-acyl amino acid such as N-lauroyl-glutamic acid derivatives. Examples of such gelling systems include those described in U.S. Pat. Nos. 3,969,087; 5,429,816; 5,733,534; 5,776,494; 5,591,424; 5,840,287; 5,843,407; 5,846,520; 5,849,276; 5,965,113; 6,190,673; and 6,241,976.

Notwithstanding the foregoing, there is still a need for improved siloxane-based polyamide gelling agents and cosmetic compositions made therefrom, especially when stick products made with such polyamides are capable of forming cosmetic products having improved clarity and physical integrity. While the importance of siliconized polyamides has been discussed in the art cited above, including a key advantage of being able to compatabilize the polyamide gelling agent with the silicone oils, there still remains a need for finding ways of forming superior products which overcome problems such as crumbling while maintaining or enhancing the aesthetics of the final cosmetic products. Moreover, it is also desired to provide clear products which are thickened with selected polyamide gelling agents, which are transparent and clear, and which can be formed into products having varying degrees of firmness, such as from a cream to a stick, depending on amounts of thickening agent contained in the composition.

Thus, it is an object of the present invention to provide an improved cosmetic composition, for example, an antiperspirant and/or deodorant stick, comprising a selected siloxane-based polyamide as a gelling agent which cosmetic composition is capable of exhibiting improved aesthetics such as clarity and which preferably leaves low to no visible white residue upon application and after drying, and especially no white residue. It is also an overall object of the present invention to provide selected siloxane-based polyamides which can be used as gelling agents to thicken cosmetic compositions, which polyamides are compatible with volatile and/or non-volatile silicone liquids and which maintain an improved degree of structural integrity to reduce cracking and crumbling while exhibiting minimum tack and better dry glide-on feel.

SUMMARY OF THE INVENTION

Clear cosmetic compositions, especially antiperspirant and/or deodorant compositions, especially clear sticks having good structural integrity, can be formed by incorporating at least 8% by weight based on the total weight of the composition of a selected siliconized polyamide as described below into a product formulated with at least one silicone fluid and at least one non-silicone emollient. The polyamides function as gelling agents to form, for example, antiperspirants and/or deodorants in stick, gel, soft solid or roll-on forms.

The siliconized polyamides useful in this invention are a subset of the polyamides represented by Formula IIIA defined below. These polyamides which are useful in this invention have the silicone portion in the acid side of the polyamide and are selected on the basis of degree of polymerization ("DP"), molecular weight, and polydispersity. In particular, (a) the DP (which pertains to the silicone portion as seen in Formula IIA below) should be in the range of 12–18, especially 15; (b) the average molecular weight of the polyamide must be at least 50,000 daltons and can range up to 200,000 daltons (particularly with a molecular weight greater than 70,000 daltons, ore particularly in the range of 80,000–150,000 (for example 80,000–90,000 daltons), and even more particularly in the range of 90,000–120,000 daltons) with at least 95% of the polyamide having a molecular weight greater than 10,000 as measured by size exclusion chromatography; (c) the polydispersity (weight average molecular weight/number average molecular weight) should be less than 20, particularly less than 10, and especially less than 4.

With regard to the stick products of this invention formulated with such polyamides, the polyamide is used with a combination of silicone and non-silicone organic materials wherein the ratio of the non-silicone organic materials to the organosilicone materials is in the range of 10:1–0.01:1.

The products of the invention are made as water in oil emulsions or water with glycol and oil emulsions and must be formulated so that for the ratio of the water phase (which may also contain a water miscible polar component such as a glycol component as described herein) to the oil phase, the ranges are 20–60% water phase: 40–80% oil phase, with a 40% water phase and 60% oil phase being preferred. The glycol component comprises one or more glycols or polyglycols selected from the group consisting of ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof. More particular examples of the glycol component include one or more members of the group consisting of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Propylene glycol is of particular interest because the antiperspirant active is more soluble in this type of glycol. Tripropylene glycol has lower irritancy, but the antiperspirant active is not as soluble in this glycol. Mixtures of glycols may be used to balance these desirable properties. Particular examples of suitable glycols include propylene glycol, dipropylene glycol, tripropylene glycol, polyglycols having a molecular weigh less than 400, and 2-methyl-1,3-propanediol.

Other parameters may also be considered. These are:
(1) degree of impurities in the siliconized polyamide;
(2) use of a particular combination of silicone, organosilicone and organic emollients; and
(3) the concentration of gellant in the formulation.

The level of impurities in the gelling agent (impurities being defined as any material having a molecular weight below 4000 daltons as measured by size exclusion chromatography) should be kept low, particularly less than 5% by weight, based on the weight of the polyamide.

The internal phase of the cosmetic composition should be comprised of at least one cosmetically active ingredient, especially a non-ethanol based antiperspirant active, and one or more members selected from the group consisting of water; polyhydric alcohols having 3–9 carbons; branched and unbranched polymeric ethers having 6–18 carbons and 5–30 ethylene oxide groups; dibenzylidene sorbitol; polyvinyl alcohol; polyvinylpyrrolidone; and mixtures of the foregoing, in which the water content is kept below 25% by weight based on the weight of the entire composition. The water phase (previously defined as optionally comprising a glycol component) must be kept in the range of 10–60% by weight based on the weight of the entire composition.

The siliconized polyamide gellant is added in the amount of 8–90 weight % and may also comprise two or more gellants which together total 10–90 weight %, provided that the final cosmetic composition is made with at least 8 weight % of a polyamide of Formula IIIA described below.

Optionally other ingredients such as silicone gums (for example P5200 and P5204 adhesion promoters from Dow Corning Corp., Midland, Mich.), elastomers (for example KSG-15 from Shin Etsu Silicones of America, Akron, Ohio.), and silicone resins (for example so-called "MQ" resins), may be used as formulation aids to achieve better structural integrity and aesthetics.

DETAILED DESCRIPTION OF THE INVENTION

The invention comprises a clear cosmetic composition which is a clear stick having a failure stress of at least 2 Pascals and which comprises:

(a) at least 8% (such as in the range of 8–18%) by weight based on the total weight of the composition of at least one siliconized polyamide of Formula IIIA:

Formula IIIA

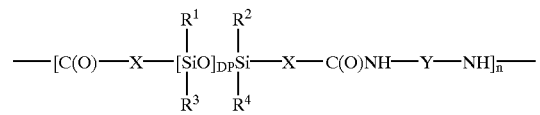

where:
(1) DP is a number in the range of 12–18;
(2) n is a number selected from the group consisting of 1–500 (particularly 20–200 and, more particularly 40–100 with an example being 40–130);
(3) X is a linear or branched chain alkylene having 1–30 carbons;
(4) Y is selected from the group consisting of linear and branched chain alkylenes having 1–40 carbons, wherein:
(A) the alkylene group may optionally and additionally contain in the alkylene portion at least one of the members of a group consisting of (i) 1–3 amide linkages; (ii) C5 or C6 cycloalkane (as a cycloalkylene linkage); and (iii) phenylene optionally substituted by 1–3 members selected independently from the group consisting of C1–C3 alkyls; and
(B) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine; or Y=Z² where

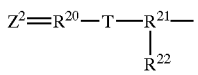

herein each of $R^{20}$, $R^{21}$ are independently selected from the group consisting of linear and branched C1–C10 alkylenes; $R^{22}$ is selected from the group consisting of linear and branched C1–C10 alkanes; and T is selected from the group consisting of (i) a trivalent atom selected from N, P and Al; and (ii) —CR, where R is selected from the group consisting of hydrogen, methyl, ethyl, propyl, isopropyl, a siloxane chain, and phenyl, wherein the phenyl may optionally be substituted by 1–3 members from the group consisting of methyl and ethyl, especially methyl and ethyl and most especially methyl; and (5) each of $R^1$–$R^4$ is independently selected from the group consisting of methyl, ethyl, propyl, isopropyl, a siloxane chain, and phenyl, wherein the phenyl may optionally be substituted by 1–3 members from the group consisting of methyl and ethyl (with more particular values for $R^1$–$R^4$ being selected from methyl and ethyl and especially methyl);

wherein the polyamide of Formula IIIA has:
(i) a silicone portion in the acid side of the polyamide;
(ii) an average molecular weight of at least 50,000 daltons (particularly in the range of 90,000–120,000) with at least 95% of the polyamide having a molecular weight greater than 10,000 daltons; and
(iii) a polydispersity of less than 20 (particularly less than 10);

(b) 5–95% (particularly 5–50% and, more particularly, 15–25%) of a silicone fluid (especially the volatile silicones such as cyclomethicone, and especially D5 cyclomethicone);

(c) 0.5–95% (particularly 5–50% and, more particularly, 10–25%) of a non-silicone organic emollient in an amount so that the ratio of non-silicone organic emollient to silicone fluid (including organosilicones) is in the range of 10:1–0.01:1;

(d) an internal phase which internal phase comprises:
(i) at least one non-ethanol based antiperspirant active; and
(ii) one or more members selected from the group consisting of water; glycol component (as hereinafter defined), polyhydric alcohols having 3–9 carbons; branched and unbranched polymeric ethers having 6–18 carbons and 5–30 ethylene oxide groups; dibenzylidene sorbitol; polyvinyl alcohol; polyvinylpyrrolidone, and mixtures of the foregoing; and
(iii) a water content below 25% by weight based on the weight of the entire composition.

The basis of the invention is the selection of certain types of polyamides and certain formulation ingredient parameters to improved antiperspirants and/or deodorant stick products which (1) are clear and (2) have improved structural integrity and aesthetics. In particular, it has been found that polyamides meeting the DP, molecular weight, and polydispersity criteria described herein provide the better gellant systems in the personal care products described below.

As noted above, the general class of polyamides from which further selections for the invention are made herein is the class generally described in copending case WO 99/06473. For the sake of clarity similar nomenclature is used here with the modifications as needed for the invention. This general description is followed by the particular description of the siliconized polyamides which give the superior results reported here. For the general description, these polyamides are multiples of a unit represented by the following Formula IIIA:

Formula IIIA

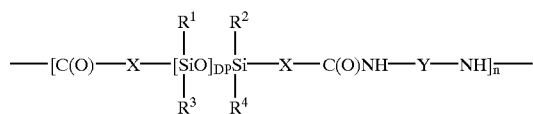

where:
(1) DP is a number in the range of 5–30, particularly 5–20, more particularly 12–18, and especially 15. DP represents an average value for degree of polymerization of the siloxane units in the polymer with greater or lesser DP values centered around the indicated DP value;
(2) n is a number selected from the group consisting of 1–500, particularly 20–200, and, more particularly, 40–100 (for example, 40–130), where n is also an average value;
(3) X is a linear or branched chain alkylene having 1–30 carbons, particularly 3–10 carbons and, more particularly, 10 carbons;
(4) Y is selected from the group consisting of linear and branched chain alkylenes having 1–40 carbons, particularly 1–20 carbons, more particularly 2–6 carbons and, especially 6 carbons, wherein:
(a) the alkylene group may optionally and additionally contain in the alkylene portion at least one of the members of a group consisting of (i) 1–3 amide linkages; (ii) C5 or C6 cycloalkane (as a cycloalkylene linkage); and (iii) phenylene optionally substituted by 1–3 members selected independently from the group consisting of C1–C3 alkyls; and
(b) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine;
or Y=Z2 where

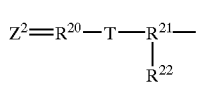

wherein each of $R^{20}$, $R^{21}$ are independently selected from the group consisting of linear and branched C1–C10 alkylenes; $R^{22}$ is selected from the group consisting of linear and branched C1–C10 alkanes; and T is selected from the group consisting of (1) a trivalent atom selected from N, P and Al; and (2) —CR, where R is selected from the group consisting of hydrogen, methyl, ethyl, propyl, isopropyl, a siloxane chain, and phenyl, wherein the phenyl may optionally be substituted by 1–3 members from the group consisting of methyl and ethyl, especially methyl and ethyl and most especially methyl; and (5) each of $R^1$–$R^4$ is independently selected from the group consisting of methyl, ethyl, propyl, isopropyl, a siloxane chain, and phenyl, wherein the phenyl may optionally be substituted by 1–3 members from the group consisting of methyl and ethyl (with more particular values for $R^1$–$R^4$ being selected from methyl and ethyl and especially methyl;

provided that in making clear cosmetic stick formulations, at least 8% of the final composition is a polyamide of Formula IIIA where the DP is in the range of 12–18 and especially 15.

The values for X, Y, DP, and $R^1$–$R^4$ may be the same or different for each unit of the polyamide.

By siloxane groups is meant groups having siloxane units:

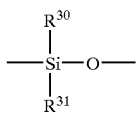

where $R^{30}$ and $R^{31}$ are each independently selected from the group consisting of organic moieties, and each of $R^{30}$ and $R^{31}$ are connected to the silicon by a carbon-silicon bond.

The carbon numbers in the alkylene chain do not include the carbons in the extra segments or substitutions. Also, the polyamides must have a siloxane portion in a the backbone

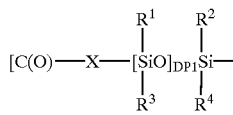

and optionally may have a siloxane portion in a pendant or branched portion.

If repeated with no variations in the defined variables, Formula IIIA is representative of a linear homopolymer. Acceptable variations of the invention include: (1) polyamides in which multiple values of DP, X, Y, and $R^1$–$R^4$ occur in one polymeric molecule, wherein the sequencing of these units may be alternating, random or block; (2) polyamides in which an organic triamine or higher amine such as tris(2-aminoethyl)amine replaces the organic diamine in part, to produce a branched or crosslinked molecule; and (3) physical blends of any of (1) and (2) and/or linear homopolymers.

Particular examples of compounds of Formula IIIA include the following:

1) Polyamides of Formula IIIA where the values for X, Y, n, and DP are the same as defined in Formula IIIA, and $R^1$–$R^4$ are each methyl;

2) Polyamides of Formula IIIA where the DP is in the range of 12–18 and the molecular weight is in the range of 90,000–120,000 daltons;

3) Polyamides of Formula IIIB:

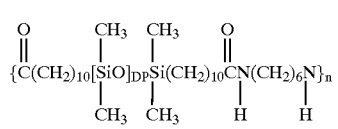

Formula IIIB where DP is from 12–18 and n has the same value as in Formula IIIA;

4) Polyamides of Formula IIIB wherein the DP is from 12–18 and the polyamide has a molecular weight in the range of 90,000–120,000 daltons;

5) Polyamides of Formula IIIB wherein the DP is 15;

6) Polyamides of Formula IIIB wherein the DP is 15 and the polyamide has a molecular weight in the range of 90,000–120,000 daltons;

7) Polyamides of Formula IIIA where the values of X, Y, DP and $R^1$–$R^4$ remain the same in each unit of the polymer;

8) Polyamides of Formula IIIB where the value of DP and n remain the same for each unit of the polymer;

9) Polyamides of Formula IIIA containing multiple siloxane block lengths as shown in Formula IIIC:

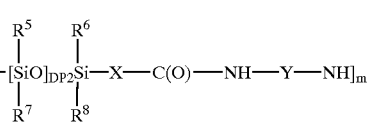

Formula IIIC where X, Y, n, and $R^1$–$R^4$ have the meanings described above for Formula IIIA; m is selected from the same groups as defined for n, and n and m denote the total number of units enclosed within the brackets, with the individual units arranged with regular, alternating, block or random sequencing; $R^5$–$R^8$ is selected from the same group as defined for $R^1$–$R^4$; DP1 and DP2 may be the same or different and are each independently selected from the same group as defined for DP; and the units denominated by n and m may be structured to form either block (regularly sequenced) or random copolymers.

10) Polyamides of Formula A containing siloxane block lengths of Formula IIIC wherein all of the R groups are selected to be methyl.

11) Polyamides of Formula IIIA containing siloxane block lengths of Formula IIIC wherein DP1=DP2.

12) Polyamides of Formula IIIA containing siloxane block lengths of Formula IIIC wherein all of the R groups are selected to be methyl and DP1=DP2.

13) Polyamides synthesized from multiple diamines as shown in Formula IIID:

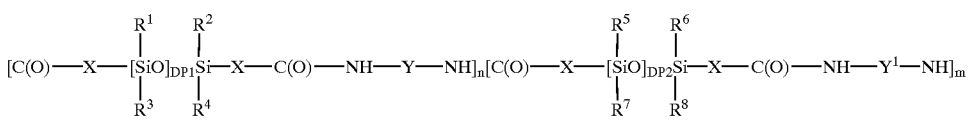

Formula IIID where X, Y, m, n, and $R^1$–$R^8$, DP1, DP2 have the same meanings as described above for Formula IIIA and Formula IIIC; $Y^1$ is independently selected from the same group as defined for Y; and the units denominated by n and m may be structured to form either block (regularly sequenced) or random copolymers.

14) Polyamides of Formula IIID where DP1=DP2.
15) Polyamides of Formula IIID where all of the R groups are selected to be methyl.
16) Polyamides of Formula IIID where all of the R groups are selected to be methyl and DP1=DP2.

Another related class of polyamides may be synthesized with trifunctional amines as shown in Formula IV:

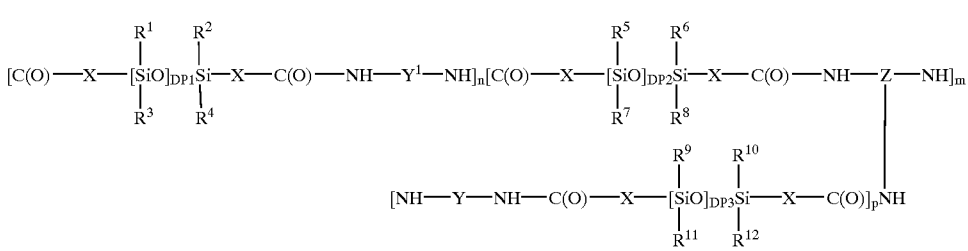

Formula IV where X, Y, $Y^1$, $R^1$–$R^8$, m, n, DP1–DP2, have the same values as defined above; $R^9$–$R^{12}$ are selected from the same group as defined for $R^1$–$R^5$, DP3 is selected from the same group as defined for DP; and p is selected from the same groups as defined for m and n;

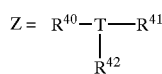

wherein $R^{40}$, $R^{41}$ and $R^{42}$ are each independently selected from the group consisting of linear and branched C1–C10 alkylenes, and T is selected from the group consisting of (1) and a trivalent atom selected from N, P and Al; and (2) CR, where R is selected from hydrogen and the same group as defined for $R^1$–$R^4$. Preferred values for p are 1–25 with more preferred values being 1–7. Preferred values for $R^1$–$R^{12}$ are methyl. A preferred value for T is N. Particular values for each of DP1–DP3 are 5–30, particularly 5–20, more particularly 12–18 and especially 15. A preferred value for each of $R^{40}$, $R^{41}$ and $R^{42}$ is ethylene. A preferred value for Z=(—$CH_2CH_2$)$_3$N.

A particular group of compounds of Formula IV are those of Formula IVA:

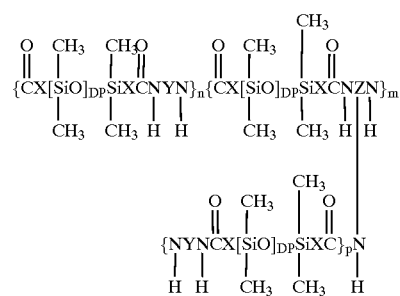

Formula IVA where X=—$(CH_2)_{10}$—, Y=—$(CH_2)_6$—; DP=12–18; m=5–20% of m+n+p; and Z=(—$CH_2CH_2$)$_3$N; m=2–500 (particularly 20–200); n=2–500 (particularly 20–200); p=2–500 (particularly 20–200); provided m=5–20% of m+n+p and m, n, and p are selected so that the average molecular weight is at least 50,000 daltons such as in the range of 50,000–200,000 daltons (particularly greater than 70,000 daltons, more particularly in the range of 80,000–150,000 (for example 80,000–90,000 daltons), and even more particularly in the range of 90,000–120,000 daltons) with at least 95% of the polyamide having a molecular weight greater than 10,000 daltons as measured by size exclusion chromatography.

In general, the siloxane-based polyamides (1) contain both siloxane groups and amide groups to thicken compositions containing silicone fluids (volatile and/or non-volatile silicone fluids); (2) are non-flowable solids at room temperature; and (3) dissolve in a fluid which contains silicone at a temperature of 25–160 degrees C to form a translucent or clear solution at a temperature in this range.

With regard to the siloxane units in the siloxane-based polyamides, the siloxane units must be in the main or backbone chain but can also optionally be present in branched or pendent chains. In the main chain the siloxane units occur in segments as described above. In the branched or pendent chains the siloxane units can occur individually or in segments.

While the invention focuses on polyamides as described above with a DP=12–18, it is noted that some amount of polyamides of the same formulae but with a DP 5–30 may be included provided that clarity and structural integrity parameters are met. Particular examples of such systems of siloxane-based polyamides include:

(a) polyamides of Formula IIIA where DP is a number in the range of 5–30, particularly 15–20, more particularly 12–18 and especially 15, provided that at least 8% of the composition is a polyamide of Formula IIIA with a DP in the range of 12–18, especially 15;

(b) physical blends of two or more polyamides described above in Formulae IIIA, IIIB, IIIC, IIID, IV and IVA, wherein (1) at least 80% of the blend is at least one polyamide as described above for this invention with a DP in the range of 5–30 with at least 8% of the final cosmetic composition being a polyamide of Formula IIIA with a DP in the range of 12–18, especially 15; and (2) the remainder of the blend is a polyamide of the Formulae IIIA, IIIB, IIIC, IIID, IV, or IVA, except that the DP value is a number in the range of 45–500, or blends of these higher DP materials;

(c) compounds of Formula IIIC where (1) the value for DP1=5–30 and the value for DP2=5–500 (more particularly, 5–100) and (2) the portion of the polyamide having DP1 is about 1–99 weight % based on the weight of the total polyamide content and the portion of the polyamide having DP2 is about 1–99 weight % with at least 8% of the final cosmetic composition being a polyamide of Formula IIIC with a DP in the range of 12–18, especially 15;

(d) physical blends of polyamides of Formula IIIB made by combining (1) 60–99 weight % of a polyamide where DP=5–30 and especially where DP=10–20, and (2) 1–20 weight % of a polyamide where DP=5–500, especially where DP=45–100 with at least 8% of the final cosmetic composition being a polyamide of Formula IIIB with a DP in the range of 12–18, especially 15;

(e) polyamides of Formula IIID where at least one of Y and $Y^1$ contains at least one hydroxyl substitution with at least 8% of the final cosmetic composition being a polyamide of Formula IIID with a DP in the range of 12–18, especially 15;

(f) polyamides of Formula IIIA synthesized with at least a portion of an activated diacid (diacid chloride, dianhydride or diester) instead of the diacid, with at least 8% of the final cosmetic composition being a polyamide of Formula IIIA with a DP in the range of 12–18, especially 15;

(g) polyamides of Formula IIIA where X=—$(CH_2)_3$— with at least 8% of the final cosmetic composition being a polyamide of Formula IIIA with a DP in the range of 12–18, especially 15;

(h) polyamides of Formula IIIA where X=—$(CH_2)_{10}$— with at least 8% of the final cosmetic composition being a polyamide of Formula IIIA with a DP in the range of 12–18, especially 15;

(i) polyamides of Formula IIIA where the polyamides are made with a monofunctional chain stopper selected from the group consisting of monofunctional amines, monofunctional acids, monofunctional alcohols, including fatty acids, fatty alcohols and fatty amines, such as, for example: octylamine, octanol, stearic acid and stearyl alcohol with at least 8% of the final cosmetic composition being a polyamide of Formula IIIA with a DP in the range of 12–18, especially 15.

Particular examples of (a)–(i) include those having a molecular weight of at least 50,000 daltons (particularly greater than 70,000 daltons, more particularly in the range of 80,000–150,000 (for example 80,000–90,000 daltons), and even more particularly in the range of 90,000–120,000 daltons) with at least 95% of the polyamide having a molecular weight greater than 10,000 as measured by size exclusion chromatography.

Polyamides of this invention can be used as a thickening agent in compositions containing silicone fluids to form creams (for example, semi-solid or soft solid), gels and sticks; thus, both soft (and mushy) or firm (and hard) compositions can be formed. The firmness of the product will depend on the amount of the gelling agent(s) used.

In general, when using polyamides of Formula IIIA to make antiperspirants and/or deodorants, an amount of polyamide equal to at least 8% by weight based on the final weight of the total antiperspirant and/or deodorant product should be used for a clear stick. This is especially true if a polyamide of Formula IIIA having a DP=15 is used. If a polyamide with a DP=30 is used, about 5–15% more polyamide must be used to obtained the same resistance to stress.

In one particular series of formulations of antiperspirant and/or deodorant products, the following table can be used to determine how much of what type of polyamide gellant of Formula IIIA to use in the final formulation. Additionally, a blend of polyamides of Formula IIIA having different DP's (in the range of 5–30) can be used, provided that there is a minimum of 8% of the polyamide having a DP in the range of 12–18 (especially 15). Examples of this are given in Table A.

TABLE A

| DP of Polyamide of Formula IIIA | DP = 12–18 (especially 15) | DP = 25–35 (especially 30) | DP = 45–50 | DP > 50 in combination with DP = 15 |
|---|---|---|---|---|
| Stick A | 8–15% | 13–20% | | at least 8% DP = 15 |
| Stick B | 8–18% | 12–20% | none | at least 8% DP = 15 |
| Stick C | 12–20% | 10–20% | | at least 10% DP = 15 |

In general, the polyamides of Formula IIIA can be produced through a condensation reaction in which a diacid is reacted with a diamine and water is removed. In this case the diacid contains siloxane groups. For example, carboxydecyl-terminated polydimethylsiloxane may be used as the diacid. Note that other organic diacids, diamines and monofunctional agents can be used in conjunction with the diacid and diamine to give modified properties. Also diacid chlorides, dianhydrides and diesters can be used instead of the diacids. One method includes using approximately equal molar amounts of the diamine and diacid.

One reaction scheme for making polyamides of Formula IIIB involves the condensation of a siloxane diacid with an organic diamine as follows:

(1) A dimethyl hydride endblocked polydimethylsiloxane is prepared containing the appropriate number of siloxane units to achieve the desired value of DP.

(2) The carboxylic acid group of undecylenic acid is protected through reaction with hexamethyldisilazane.

(3) The dimethyl hydride endblocked polydimethylsiloxane and the protected undecylenic acid (the products of Steps (1) and (2)) are reacted to produce a siloxane diacid (carboxydecyl terminated polydimethylsiloxane). This reaction is accomplished in the presence of a platinum catalyst such as chloroplatinic acid, and the product is washed with methanol to remove the trimethylsilyl protecting group.

(4) The siloxane diacid (product of Step (3)) is reacted with an organic diamine to produce a siloxane-based polyamide. This reaction may involve the use of reaction solvent such as toluene or xylene. U.S. Pat. No. 6,051,216 describes such a reaction scheme.

It should also be noted that nomenclature is being developed to call this type of polyamides "nylon/dimethicone copolymers" such as "nylon 611/dimethicone copolymer", where "611" means that the organic portion of the copolymer has 6 and 11 carbons on either side of the amide group.

While one method for making polyamides is described in U.S. Pat. No. 6,051,216 listed above, another method for making such polyamides is described in U.S. Pat. No. 5,981,680, both of which are incorporated by reference as to the methods of making such compositions. The process of U.S. Pat. No. 5,981,680 involves the addition of an olefinic acid with an organic diamine to product an organic diamide. Once the olefinic acid and the organic diamine are fully reacted, an =SiH endblocked polysiloxane is added in the presence of a platinum catalyst to product a siloxane-based polyamide via hydrosilylation.

As noted above, the two major factors in describing the polyamides of this invention are DP and molecular weight. Optimal polymers are formed from the reaction of a siloxane diacid with a DP=5–30, more particularly 12–18, and especially 15, and an organic polyfunctional amine (for example, hexamethylenediamine). (Note that the five-step method uses a siloxane diacid with a diamine and a three-step method (see U.S. Pat. No. 5,981,680) use siloxane plus diamide.) Polymers having molecular weights ("MW") in the range of 4,000–200,000 may be produced, especially those in the range of 50,000–150,000. Reference is made to U.S. Pat. No. 6,051,216 and U.S. patent application Ser. No. 9/873,504 described above for methods that may be used to obtain such polymers. Reference is also made to a U.S. patent application filed on Jul. 12, 2001, by Dow Corning Corporation as their Docket No. DC4882 which is incorporated by reference herein as to its method of making selected polyamides. This most recent case uses a siloxane and diamide method which is improved by the attention directed to chain terminators and reactant ratios. It is believed that this most recent case, at the very least, describes a commercially more efficient way of producing polyamides described for this invention, especially in the range of 80,000–150,000 daltons, particularly 80,000–120,000 daltons (with a particular example being 80,000–90,000 daltons), and more particularly 90,000–120,000 daltons.

Polyamides having a molecular weight in the range of 90,000–120,000 daltons and a degree of polymerization (DP) in the range of 12–18, especially 15, are especially useful in practicing the invention.

Optimizing the length of the siloxane portions of the molecule (the "DP") involves a balancing of various considerations. Polyamides with long siloxane chains (for example, DP>50) tend to produce soft gels in cyclomethicone. The efficiency of the gellant is improved by reducing the length of the siloxane units (that is, selecting and making a molecule with a DP<50), but the compatibility with cyclomethicone may be compromised as the DP decreases. For example, a polyamide synthesized from a siloxane diacid with a DP=15 and hexamethylene diamine does not produce clear gels in cyclomethicone. However, transparent gels can be obtained if an organic emollient such as, for example, PPG-3 myristyl ether or isoparaffins is blended at various levels with the silicone fluids. As a result, polymers with DP=15 are preferred, so that the formulation for the resulting cosmetic composition has a combination of some compatibility with silicone fluids and good gelling efficiency. It should be noted that frequently more than one emollient is normally used to achieve the preferred aesthetics, and transparency, for example, with a DP=15.

In addition to the DP of the polyamide, the molecular weight must also, be considered. Polymers of extremely high molecular weight (for example, greater than 200,000 daltons) tend to produce rubbery, elastic gels and are less desirable. It has been found that optimal gellation occurs with polyamide gellants of molecular weight greater than 70,000 (particularly in the range of 90,000–120,000 daltons) as determined by size exclusion chromatography with universal calibration as described in Styring, J. E. et al "An Experimental Evaluation of a New Commercial Viscometric Detector for Size-Exclusion Chromatography (SEC) Using Linear and Branched Polymers," *J. Liquid Chromatography*, Volume 9, pages 783–804 (1986). In practicing the current invention, the optimal range of molecular weights for the primary gellant should be from 50,000–150,000 daltons, especially 70,000–120,000 daltons, and more especially 80,000–150,000 daltons, particularly 80,000–120,000 daltons (with a particular example being 80,000–90,000 daltons), and more particularly 90,000–120,000 daltons. It is believed, however, that incorporation of low levels of such high molecular weight species, for example, 0.5 weight % of a high molecular weight polyamide having a molecular weight in the range of 120,000–200,000 may give the base composition and cosmetic compositions made therefrom improved mechanical properties. Overall it is desired that at least 95% of the siliconized polyamide gellant have a molecular weight of at least 10,000 daltons.

It has been found that selecting siliconized polyamides with certain values for polydispersity and suitable stress/strain properties has an important affect on being able to form stick products. Polydispersity is calculated as $M_W/M_N$ where $M_N$ is number average molecular weight and $M_w$ is weight average molecular weight. More particularly, when the molecular weight of the siliconized polyamide is increased while the polydispersity of the polyamide gellant remains narrow, the strength of the formulated product increases. The strength of the formulated product is monitored using a Three Point Bending technique as found in *An Introduction to the Mechanics of Solids,* (edited by Lardner, T. J.; McGraw-Hill 1978). A failure stress greater than 2.0 Pascals (and preferably greater than 4.0 Pascals) is desired for a stick product. If the failure stress is less than 2.0 Pascals, a softer stick can be formed.

As noted above, the siloxane-based polyamides used as thickening agents in base and cosmetic compositions of the present invention contain both siloxane units and amide linkages. The siloxane units provide compatibility with the silicone fluid (for example with the cyclomethicones), while the amide linkages and the spacing and selection of the locations of the amide linkages facilitate gellation and the formation of cosmetic products. While opaque as well as clear compositions may be formed, it is preferred that the cosmetic compositions formed be clear upon cooling a solution of a combination of the siloxane polyamide with the silicone and organic emollient component and leaves low to no white residue after application to the underarm area.

For antiperspirants and/or deodorants made with the type of gellant described here, emulsion or suspension stick products may be formed. If an emulsion is formed, characteristically it is with an internal phase and an external phase. The external phase is defined as the continuous phase where liquids are interconnected. The internal phase is defined as the suspended phase where liquids exist in a droplet form stabilized by surfactants. In the case of antiperspirant emulsion formulations, the external phase is the gelled oil phase and the internal phase contains the antiperspirant active. The external gelled oil phase contains at least one silicone fluid, at least one non-silicone organic emollient, and the siloxane-based polyamide gellant, as well as optional additives for the antiperspirant product such as surfactants, fragrances, additional emollients etc. The internal phase consists of a liquid solution containing dissolved antiperspirant salt, and typically involves solvents such as water, propylene glycol, dipropylene glycol, tripropylene glycol, ethanol, 1,2-hexanediol.

The siloxane-based polyamide gelling agent, can consist of one or more polyamides as described above (or a mixture of these polymers) as the sole gelling agent, or can contain the polyamide admixed with other thickening agents (including conventional gelling agents). The siloxane units provide compatibility with the silicone fluids. The amide portions are utilized reversibly for physically cross-linking purposes so as to form the gel.

With regard to the external or oil phase, an additional component such as 12-hydroxystearic acid, N-acyl-glutamic acid diamide, amine stearate, N,N'-hexamethylene-bis-(10-undecenamide), silica, materials known as "M/Q resins" as described herein, (particularly any of the foregoing in bead form) may be added to the oil phase (for example, to enhance the strength of the final formulation). Normally these types of ingredients would be added in the external phase.

In selecting any of the components which form the basis of the invention or any of the additional components which may optionally be included, care must be taken to preserve the clarity of the product. In particular, the following ingredients (which may be used as co-gellants) are particular examples of materials that may be used with minimal impact on clarity: <1.7% dibenzylidene sorbitol (only in anhydrous systems); <0.5% 12-hydroxy stearic acid; <0.5% amine stearate; <0.5% N,N'-hexamethylenebis-(10-undecenamide; <5.0% silicone elastomer (for example, DC-9040 form Dow Corning Corp. or KSG-15 from Shin-Etsu); and <0.5% N-lauroyl glutamic acid amide (for example, GP-1 from Ajinomoto).

The formulations of this invention are emulsions wherein the antiperspirant active phase (internal phase) is made by dissolving solid particles of active ingredient in either water or a water/glycol mixture. These solid particles may be antiperspirant salt powders (such as aluminum chlorohydrate or aluminum zirconium tetrachlorohydrex glycine or others as described herein) and may contain water levels of 0–75 weight %. At the higher water levels (for example, >50% water) some gellation promoter (such as ammonium acetate) may be required to provide rigidity to these aqueous droplets. After the emulsion is formed, the emulsion droplets are dispersed in a carrier comprising cosmetically acceptable ingredients such as silicones, organic emollients and at least one siliconized polyamide that fits the criteria described for this invention.

If a clear antiperspirant and/or deodorant product is desired, the two phase system is preferably used with matching of refractive indices of the external and internal phases. Microemulsions can also be used to achieve clear products, but it is not required.

It has also been found that when water is used as the internal phase (in a solution of water and antiperspirant active) the cracking and/or crumbling of the formula is the most severe and the cosmetic composition itself has more drag upon application to the skin. As the amount of water is increased the stick form is more brittle. In contrast to this, when a non-water or reduced water system is used as the internal phase (such as propylene glycol, also in a solution containing antiperspirant active), the brittleness of the cosmetic composition decreases. Thus, it is preferred to use a non-water internal phase such as propylene glycol in an amount of 5–50%, more preferably from 35–45%. In addition, other thickeners such as one or more of silica, dibenzylidene sorbitol (only in anhydrous systems), and polyvinyl alcohol may be added to the propylene glycol or water in the internal phase containing antiperspirant active; such additional ingredients will also help to enhance the strength of the final composition.

In contrast to the co-pending case referenced above as U.S. Provisional application No. 60/229,444, which may contain antiperspirant active added as powders which improve structural integrity, this invention adds the active as a solution, so that it is harder to maintain structural integrity. Again in contrast to the co-pending case 60/229,444 which describe opaque to translucent products, the products of this invention are clear yet still provide low to no white residue.

The gels of the present invention include silicone fluids. These fluids can be volatile or non-volatile and include linear siloxanes known as dimethicones, linear siloxanes containing an aromatic substitution such as phenyl trimethicone and the various cyclic siloxanes having from 4–6 siloxane units in a ring optionally substituted by C1–C6 alkyl or phenyl, particularly cyclic dimethyl siloxanes such as cyclomethicones. Mixtures of such silicone fluids may also be used. Suitable volatile silicone liquids are described in U.S. Pat. No. 5,102,656 to Kasat, referenced above. Examples of other known silicone fluids for use in cosmetic compositions are disclosed in U.S. Pat. No. 4,853,214 to Orr, referenced above and are suitable for use in this invention. Other particular examples include linear volatile silicone fluids, for example, silicone liquids conventionally used in cosmetic compositions. One particular group is illustratively (and not of a limiting nature), phenyl trimethicone, cyclomethicones and/or dimethicones, and silanols such as those described in U.S. Pat. No. 5,871,720, incorporated by reference herein to the extent these compounds are described.

Preferably, the silicone fluid includes cyclomethicones. The cyclomethicone used (that is, ring size of the cyclomethicone) has an effect on the hardness of the gels formed. That is, cyclomethicone having five siloxane units produces a softer gel than that produced utilizing a material with 6 siloxane units. As the ring size of the cyclomethicone increases, the rigidity of the gel system formed increases. As described above, particular examples of suitable cyclomethicones include those having rings of 4–6 siloxane units, especially "D5".

The cosmetic compositions may include from 0–25% (preferably 10–20%) of an organosilicone that is selected from Formula IA (or mixtures thereof):

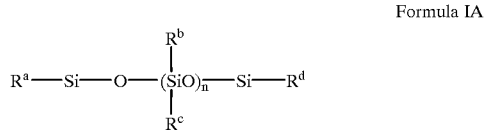

Formula IA wherein each of $R^a$, $R^b$, $R^c$, and $R^d$ may be the same or different and are each independently selected from the group consisting of hydrogen, C1–C15 alkyl, phenyl, and C1–C15 alkyl itself containing a member selected from the group consisting of —OH, —COOH, —NH$_3$—CO(O)—, and n is a number in the range of 5–500. A particular set of examples of Formula IA include those wherein each of $R^a$, $R^b$, $R^c$, and $R^d$ may be the same or different and are each independently selected from the group consisting of hydrogen, C1–C15 alkyl (for example, methyl, ethyl, propyl, isopropyl), phenyl, and C1–C15 alkyl itself containing a member selected from the group consisting of, —OH, —COOH, —NH$_3$, —CO(O)—, and n is a number in the range of 5–500. Examples of compositions of Formula IA include phenyltrimethicone, caprylyl methicone, and phenethyl dimethicone.

Suitable functionalized silicone fluids are hydroxy functional fluids with the general structure of Formula V:

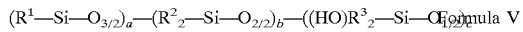

Formula V where
each of $R^1$, $R^2$, and $R^3$, may be alike or different and are each independently selected from the group consisting of C1–C4 straight chain alkyls (especially methyl);
a is a number in the range of 0–10, with particular values of "a" being 0 for linear compounds and 1–10 for branched compounds (for example 6–8);
b is a number in the range of 0–10,000, with particular values of "b" being 4–6000;
c is a number in the range of 1–10, with particular values of "c" being 2 when the compound is linear and at least 3 when there is branching; provided that a and b cannot both equal zero at the same time. It is to be recognized that a, b, and c are average values (including whole numbers and fractions) and mixtures of compounds with various values for a, b, c, $R^1$, $R^2$, and $R^3$ may also be used.

Examples of compounds of Formula V include:
(a) linear polydimethylsiloxanediols where a=0, b=4–6,000 (for example, an average value of 4, 40 or 6,000);
(b) linear polydimethylsiloxanediols where a=0, b=4–1,000 and c=2;
(c) multifunctional branched siloxanes where a=1–2, b=0–1,000, and c=3–4;
(d) linear polydimethylsiloxanediols where a=0, b=40 and c=2;
(e) multifunctional branched siloxanes where a=1, b=16, and c=3;
(f) multifunctional branched siloxanes where a=1–2, b=10–1,000, and c=3–4;
(g) mixtures of the particular compounds described in parts (a)–(f), for example, mixtures wherein the average structure of the mixture is described by a=0.1, b=4–6000, and c=2–7; and
(h) two component mixtures of the particular compounds described in parts (a)–(f) wherein one component is 0.1–99.9% of the composition and the other component is the remainder to 100%.

For each of the groups listed as (a)–(f) above, particular examples of the compounds are when each of the R groups is selected to be methyl. Also, for any of the groups (a)–(g), additional silicone fluids such as dimethicone may be added, for example in amounts of 0.1–90% functionalized silicone and 10–99.9% silicone fluid or fluids.

One particular group of compounds of Formula V are linear silanols of Formula VA, especially when b=40:

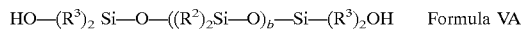

Formula VA

Some of the compounds of Formula V may be purchased commercially. For methods of making other compounds of this invention descriptions of suitable methods may be found in the literature for example, U.S. Pat. No. 5,302,382 to Dow Coming; U.S. Pat. No. 3,441,537 to Stauffer Chemical Company; and Noll, W., *Chemistry and Technology of Silicones*, (Academic Press, Inc. Orlando, Fla. 1968) especially at pages 190–196 and 239–245, all of which are incorporated herein by reference to the extent they describe how to make these compounds.

While the hydroxy functionalized silicones described above are preferably selected to have a viscosity that does not require additional silicone materials (for example, having a viscosity in the range of up to 60,000 centistoke (cst), it is possible to use compositions which are a blend of hydroxy functionalized silicones having higher viscosities such as those having a high viscosity (>500,000 centistoke) dimethiconol in dimethicone where the dimethicone has a viscosity in the range of 5–350 centistoke (for example, DOW CORNING® 1403 Fluid).

For high viscosity functionalized silicones (for example, the silicone gums), and for the purpose of facilitating its handling and processing, these materials are generally provided as blends with another volatile or non-volatile low viscosity silicone such as CYCLOMETHICONE, or a non-volatile linear silicone fluid having a viscosity of about 5 to 350 centistoke. Such dimethyl silicone polymers terminated with hydroxyl groups have been assigned the INCI name "DIMETHICONOL" by The Cosmetics, Toiletries and Fragrance Association, Inc., Washington, D.C. (CTFA). Blends of such silicone gums with a volatile low viscosity cyclic silicone have been assigned the INCI name "CYCLOMETRICONE (and) DIMETHICONOL" by the CTFA. Other blends of such silicone gums with a non-volatile low viscosity linear silicone have been assigned the INCI name "DIMETBICONE (and) DIMETHCONOL" by the CTFA. The DIMETHICONOL content of such blends is typically in the range of about 12 to 14 percent by weight, and the blend viscosity may range from 500 to about 20,000 centistoke, generally in the range of about 4,000 to 5,000 centistoke. DIMETICONE concentrations in the range of 10–48% are known or may be made from other concentrations.

Other volatile low viscosity methylsilicone fluids are described in U.S. Pat. No. 5,302,382 to Kasprzak, incorporated by reference herein. Examples of methylsilicone fluids having viscosities of less than about one hundred centistoke measured at twenty-five degrees Centigrade, preferably less than about two centistokes and also methylsilicone fluids having a viscosity in the range of 1–350 centistoke are disclosed.

One group of methylsilicone fluids is volatile low viscosity methylsilicone fluid containing dimethylsiloxane units and, optionally, trimethylsiloxane units.

Representative compounds are cyclopolysiloxanes of the formula $[(CH_3)_2SiO]_x$, and linear short chain siloxane compounds of the formula $(CH_3)_3SiO[(CH_3)_2SiO]_ySi(CH_3)_3$, in which x is an integer having a value of from three to ten, (especially 4–6) and y is an integer having a value of from zero to about four. The cyclopolysiloxanes have been assigned the INCI name "CYCLOMETHICONE" by The Cosmetics, Toiletries and Fragrance Association, Inc., Washington, D.C. (CTFA).

The silicone fluid phase can also, optionally, include other silicone materials even when the purpose is for reasons other than viscosity modification. Particular silicone fluids are selected so that a stable emulsion can be formed when the two phases are combined and mixed. Such materials can include, for example, other silicone fluids such as polydimethylsiloxanes, polydiethylsiloxanes, and polymethylethylsiloxanes, having a viscosity in excess of 350 centistoke and up to 2,500,000 centistoke, preferably, 350–10,000 centistoke. Further examples include cetyl dimethicone copolyol, dimethicone copolyol (such as DOW CORNING® 2501, Q2-5220 and 5324 products); a mixture of cyclomethicone and dimethiconol (such as DOW CORNING® 1401 product); a mixture of dimethicone and dimethiconol (such as DOW CORNING® 1403 product); cetyl dimethicone (DOW CORNING® 2502 product); and stearyl dimethicone (DOW CORNING® 2503 product).

The non-silicone emollients which may be used in this invention are those which are either themselves or in mixtures with other solvents miscible in the originally selected silicone fluid (for example, C14–C20 straight or branched chain fatty alcohols (especially isostearyl alcohol and octyldodecanol)), isopropyl myristate, PPG-3 myristyl ether, octyl salicylate, isoparaffins, dioctyl ether, PPG-10 cetyl ether, octyl methoxycinnamate), and C12–15 alkyl benzoate (for example, FINSOLV TN from Finetex Inc., Elmwood Park, N.J.).

Compositions according to the present invention desirably include silicone-miscible emollients. Illustrative emollients, which are not limiting of the present invention, would include guerbet alcohols (such as isocetyl alcohol or isostearyl alcohol); esters having 14–22 carbons (such as isopropyl palmitate, isopropyl isostearate, octyl stearate, hexyl laurate and isostearyl lactate); and a liquid mixture of hydrocarbons which are liquids at ambient temperatures (such as petroleum distillates and light mineral oils). The silicone-miscible solvents (also called emollients) can be included in the compositions of the present invention in amounts within the range of 0–70%, preferably 5–25%, by weight, of the total weight of the composition.

The internal phase comprises at least one active ingredient in an amount sufficient to have a functional effect. Such actives include, but are not limited to fragrances, sunscreens, antiperspirants, deodorants and antibacterials (antimicrobials). For example, where the composition is a composition to protect skin from the sun, a sufficient amount of a sun-screening agent is provided in the composition such that when the composition is applied to the skin, the skin is protected from the harmful effects of the sun (for example, is protected from ultraviolet rays from the sun).

The external phase composition is combined with an internal phase, which internal phase comprises at least one active ingredient and other optional ingredients such as fragrance, emollients (especially silicone-miscible emollients), coloring agents, fillers, antibacterials (antimicrobials) and other conventional ingredients known to those in the art for formulating such products to form cosmetic compositions.

In stick products made according to this invention, the polyamide gelling agent can be used in an amount of 8–80 percent by weight, more particularly 8–30%, even more particularly 8–20% and, most particularly, 10–15 percent by weight based on the total weight of the composition. It is preferred that the gellant not exceed 50 percent by weight of the base composition. The silicone fluid portion is in the range of 5–95 percent by weight, more particularly 10–80 percent by weight, even more particularly 10–40 percent by weight.

A cosmetically active ingredient is also added to the composition. Various cosmetically active materials incorporated in cosmetic compositions are disclosed in U.S. Pat. No. 4,322,400 to Yuhas, the contents of which are incorporated herein by reference in their entirety to the extent these materials are described.

In one particular aspect of the invention, deodorant and/or antiperspirant compositions, in the form of sticks, which have high efficacy, an attractive appearance (for example, which can be clear or at least translucent), and preferably which are made to leave substantially low to no visible white residue upon application or upon drying, can be achieved.

Throughout the present specification, "antiperspirant active" and "deodorant active" materials are discussed. Both types of materials contribute to reduction of body malodor, for example, axillary malodor. By reduction of body malodor, it is meant that, generally, there is less body malodor after application of the composition to a person's skin, as compared to a person's malodor without application of the composition. Such reduction can be due to a masking of the malodor, absorption and/or chemical reaction of the malodorous material, reduction of the levels of the bacteria producing the malodorous materials, for example, from perspiration, reduction of perspiration, etc. The antiperspirant active materials, when utilized in appropriate amounts, primarily act to reduce malodor by reducing perspiration; the antiperspirant active materials can also have a deodorant function, for example, as an antimicrobial or bacteriostatic agent. The deodorant active materials do not substantially reduce perspiration, but reduce malodor in other ways. For example, as fragrances masking the malodor or reducing the malodor intensity; absorbents; antimicrobial (bacteriostatic) agents; or agents chemically reacting with malodorous materials.

Where the composition contains an antiperspirant active, any of the known antiperspirant active materials can be utilized. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention.

Antiperspirant actives can be incorporated into compositions according to the present invention in amounts in the range of 0.1–25%, 5–25 percent, and preferably 15–25%, by weight, of the total weight of the composition. The amount used will depend on the formulation of the composition. For example, at amounts in the lower end of the broader range (for example, 0.1–10%), the antiperspirant active material will not substantially reduce the flow of perspiration, but will reduce malodor, for example, by acting as an antimicrobial material.

Where the composition is an antiperspirant composition, the composition can also include a solvent for the antiperspirant active. This solvent, which is not miscible with the silicone fluid, can illustratively be water, propylene glycol, dipropylene glycol, tripropylene glycol butylene glycol, 1,2-hexanediol, dimethyl isosorbide, polyhydric alcohols having 3–9 carbons, polymeric ethers having 5–30 units selected from the group consisting of ethylene oxide and propylene oxide.

Where the antiperspirant active is utilized in a solution, it may be necessary to match refractive indices of the antiperspirant active solution with that of the oil portion of the composition, in order to achieve a transparent or clear composition. Where the antiperspirant active material is suspended in the base composition as particulate material, it may also be necessary to match refractive indices of the active material and base composition to obtain a clear or transparent composition as described above. Such refractive index matching is a technique known in the art, and is shown in PCT (International Application) Publication No. WO 92/05767, the contents of which have previously been incorporated herein by reference in their entirety. The solvent for the antiperspirant active material can be included in the composition in an amount within the range of 0–75%, preferably 0–30%, by weight, of the total weight of the composition.

When an antiperspirant active is used, the compositions of the present invention can also be utilized to form clear antiperspirant compositions. In a particular embodiment the refractive indices of the external and internal phases are matched (within 0.005) using techniques known in the art.

Where deodorant active materials are incorporated in compositions according to the present invention, so as to provide deodorant compositions, conventional deodorant fragrances and/or antimicrobial agents can be incorporated as the deodorant active materials. A fragrance would, illustratively, be incorporated in an amount of 0.5%–3.0% by weight, of the total weight of the composition. Known bacteriostats include bacteriostatic quaternary ammonium compounds such as 2-amino-2-methyl-1-propanol (AMP), cetyl-trimethylammonium bromide, cetyl pyridinium chloride, 2,4,4'-trichloro-2'-hydroxydiphenylether (Triclosan), N-(4-chlorophenyl)-N'-(3,4-dichlorophenyl) urea (Triclocarban) and various zinc salts (for example, zinc ricinoleate). The bacteriostat can, illustratively, be included in the composition in an amount of 0.1–1.0% by weight, of the total weight of the composition. Triclosan, can illustratively be included in an amount of from 0.1% to about 0.5% by weight, of the total weight of the composition.

Compositions according to the present invention can include other cosmetic additives conventionally incorporated in cosmetic compositions, including (but not limited to) perfumes, cosmetic powders, colorants, emulsifiers, emollients, organosilicones, fatty esters, behenoxy dimethicone, etc. and other cosmetic agents. As for various other ingredients which can be incorporated, attention is directed to the optional components such as colorants, perfumes and additives described in the following U.S. Patents: U.S. Pat. No. 5,019,375 to Tanner, et al (the contents of which are incorporated herein by reference in their entirety); U.S. Pat. No. 4,937,069 to Shin (the contents of which are incorporated herein by reference in their entirety); and U.S. Pat. No. 5,102,656 to Kasat (the contents of which have been previously been incorporated herein by reference in their entirety). The use of optional additives may, of course, adversely affect clarity.

Cosmetic compositions according to the present invention can also include surface active agents and/or solvents for the cosmetically active material. For example, where the composition is an antiperspirant composition, containing antiperspirant active material, the antiperspirant active material can be included in the composition in a solution in, for example, water, and/or propylene glycol, which may not be miscible with the silicone fluid, and the composition can also include surface active agents so as to disperse the solution of antiperspirant active material in the composition. Where the composition according to the present invention is a deodorant composition, the composition can include conventional fragrances and/or antibacterial (antimicrobial) agents as deodorant active materials.

Additives may be added to the base composition to help add and incorporate active ingredients, improve mechanical properties, improve aesthetic properties, make a clear product, make a product with color, etc. Thus, cosmetic compositions may then be made by combining the base composition with one or more additional components, active ingredients, one or more vehicles to allow the active ingredient to combine more easily (or with more desirable properties) with the base composition, and other ingredients used by those in the art to formulate cosmetically acceptable products including fragrances, emollients, antibacterials hardeners, strengtheners, chelating agents, colorants, emulsifiers and other additives such as, silicas, silica-based resins, fumed silica, high molecular weight polymers (for example silicone gums, elastomers).

Optionally, additional solvents, mixtures of solvents or cosmetic additives may also be added to the base composition. Such additional ingredients can be used in amounts of 0.1–85 percent, more particularly 0.1–75 percent and, even more particularly, 0.1–55 percent where the percentages are based by weight on the total composition as 100 percent. The lower percent ranges include formulations where only fragrances or antimicrobials are used, and the upper ranges include formulations containing active antiperspirant ingredients.

Compositions according to the present invention are thermoreversible gels; that is, the gels are formed by cooling a solution of the polymer in the silicone fluids, but the gel can be broken (formed back into a liquid) by heating the gel.

The solvent for the thickening agent (which thickening agent will include at least one polyamide as described above) is included in the composition in an amount sufficient such that the thickening agent can be dissolved therein and gelled therefrom, and includes a silicone fluid (for example, a silicone oil, such as cyclomethicone and/or dimethicone). Thus, the thickening agent can be dissolved in the solvent and gelled therefrom, for example, upon cooling the composition during manufacture thereof. The solvent is not limited to those materials containing only a silicone fluid, and can contain other solvents for the thickening agent as long as such other solvents are compatible with, for example, the active cosmetic material and do not disadvantageously affect, for example, clarity of the composition, especially where it is desired to provide a clear cosmetic composition. Illustratively, and not to be limiting, the solvents can include:

(a) esters (for example, isopropyl myristate and C12–15 alkyl lactate);
(b) silicone fluids (for example, cyclomethicone, dimethicone);
(c) guerbet alcohols having 8–30 carbons, particularly 12–22 carbons (for example, isolauryl alcohol, isocetyl alcohol, isostearyl alcohol);
(d) fatty alcohols (for example, stearyl alcohol, myristyl alcohol, oleyl alcohol, isocetyl alcohol);
(e) ethoxylated and propoxylated alcohols (for example, the polyethylene glycol ether of lauryl alcohol that conforms to the formula $CH_3(CH_2)_{10}CH_2(OCH_2CH_2)_bOH$ where b has an average value of 4 (also called laureth –4); PPG-14 butyl ether, where the "PPG-14" portion is the polymer of propylene oxide that conforms generally to the formula $H(OCH_2C(CH_3)H)_cOH$, where c has an average value of 14; PPG-3 myristyl ether which is the polypropylene glycol ether of myristyl alcohol that conforms to the formula $CH_3(CH_2)_{12}CH_2(OCH(CH_3)CH_2)_dOH$ where d has an average value of 3; PPG-10 cetyl ether which conforms to the formula $CH_3(CH_2)_{14}CH_2(OCH(CH_3)CH_2)_eOH$, where e has an average value of 10;
(f) dioctyl ether;
(g) octylmethoxycinnamate and octyl salicylate;
(h) C12–C18 alkyl benzoate (especially C12–C15 alkyl benzoate) and benzoate ester derivatives thereof (for example, isostearyl benzoate and octyl dodecyl benzoate);
(i) isoparaffins having a distillation temperature in the range of 178–207 degrees C.;
(j) dioctyl carbonate; and
(k) paraffins having a distillation temperature in the range of 372–426 degrees C.

Mixtures of solvents can also be used. Of course, the gelling agent must be soluble in the solvent system, at least at elevated temperatures, as described in U.S. Pat. No. 5,500,209.

Where a multi-phase system is utilized as the composition of the present invention, preferably the composition includes a surfactant or surfactant blend. Surfactants illustratively include alkanolamides (such as N-alkyl pyrrolidone), ethoxylated amides (for example, the polyethylene glycol amide of tallow acid that conforms generally to the formula $RC(O)—NH—(CH_2CH_2O)_nH$ where RCO-represents the fatty acids derived from tallow and n has an average value of 50 (also called PEG-50 tallow amide)); amine oxides (for example, cocamidopropylamine oxide); ethoxylated carboxylic acids (for example, the polyethylene glycol diester of lauric acid that conforms generally to the formula $CH_3(CH_2)_{10}C(O)—(OCH_2CH_2)_nO—C(O)(CH_2)_{10}CH_3$ where n has an average value of 8 (also called PEG-8 dilaurate)); ethoxylated glycerides (for example, a polyethylene glycol derivative of Castor Oil with an average of 4 moles of ethylene oxide (also called PEG-4 castor oil)); glycol esters (for example, propylene glycol ricinoleate); monoglycerides (for example, glycerol myristate); polyglyceryl esters (for example, polyglyceryl-4 oleyl ether); polyhydric alcohol esters and ethers (for example, sucrose distearate); sorbitan/sorbitan esters (for example, sorbitan sesquiisostearate); triesters of phosphoric acid (for example, trioleth-8 phosphate (a material which is predominantly the triester of phosphoric acid and ethoxylated oleyl alcohol with an average of 8 moles of ethylene oxide)); ethoxylated alcohols (for example, laureth-4); ethoxylated lanolin (for example, a polyethylene glycol derivative of Lanolin with an average of 20 moles of ethylene oxide (also called PEG-20 lanolin)); ethoxylated polysiloxanes (for example, dimethicone copolyol); propoxylated polyoxyethylene ethers (for example, the polyoxypropylene, polyoxyethylene ether of cetyl alcohol that conforms generally to the formula $CH_3(CH_2)_{14}CH_2(OCH(CH_3)CH_2)_x(OCH_2CH_2)_yOH$ where x has an average value of 5 and y has an average value of 20 (also called PPG-5 ceteth-20)); and alkylpolyglycosides (for example, lauryl glucose). The surfactant (or surfactant blend) includes non-ionic compounds, and can also include blends thereof with cationic (for example, the polyethylene glycol amine of tallow acid that conforms generally to the formula R—NH—(CH$_2$CH$_2$O)$_n$H (also called PEG-15 tallow amine)) or anionic (for example, sodium lauroyl isethionate which is the sodium salt of the lauric acid ester of isethionic acid) surfactants.

The surfactant or blend thereof incorporated in compositions according to the present invention can, illustratively, be included in amounts of 0–15%, preferably 1–10%, by weight, of the total weight of the composition.

The MQ resins suitable for use with this invention may be represented by Formula IIA:

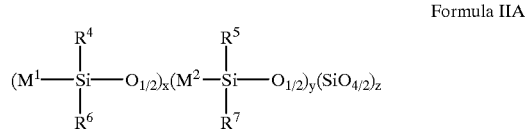

Formula IIA wherein

R$^4$, R$^5$, R$^6$, and R$^7$ are each independently selected from the group consisting of phenyl and C1–C12 branched and unbranched hydrocarbons, particularly C1–C12 branched and unbranched alkyl, more particularly branched and unbranched C1-C5 alkyl and especially methyl;

M$^1$ and M$^2$ are each independently from the group consisting of
  (a) hydrogen,
  (b) phenyl,
  (c) phenethyl,
  (d) a polyether of Formula IIB:

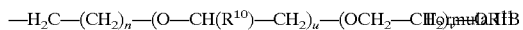

where n is a number from 1–20 and the —(CH$_2$)— chain may optionally contain 1 or 2 unsaturations; u and v are integers each independently selected from 0–20, provided that u+v≧1; R$^{10}$ is selected from C1–C20 alkyl; and R$^{11}$ is selected from the group consisting of H, —CH$_3$ and —C(O)CH$_3$; and
  (e) C1–C24 branched and unbranched hydrocarbons optionally substituted by a halogen substituted C1–C3 hydrocarbon radical, with a particular value for R$^2$ being C1–C24 alkyl, especially methyl.

wherein (x+y)/z is a number in the range of 0.5 and 1.5, and is preferably equal to 1; and the values for R$^4$, R$^5$, R$^6$, R$^7$, x, y, z, M$^1$ and M$^2$ are selected to so that the MQ resin is a liquid having a viscosity of 1.0×10$^3$–1×10$^6$ centipoise, such as 1.5× 10$^3$–1×10$^6$ centipoise.

A particular type of MQ resin of Formula IIA when x and y are the same may be represented by Formula IIC:

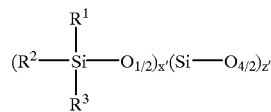

Formula IIC wherein R$^1$ and R$^3$ are each independently selected from the same group as defined for R$^4$, R$^5$, R$^6$ and R$^7$ of Formula IIA; R$^2$ is selected from the same group as described for M$^1$ and M$^2$ and x'/z' is a value between 0.5 and 1.5.

As indicated previously, the compositions according to the present invention are sticks with varying degrees of rigidity depending on amounts of thickening agent incorporated in the composition. It is difficult to quantitatively distinguish between a cosmetic "gel" and a cosmetic "stick". Generally, a gel is more viscous than a liquid or than a paste which fails to retain its shape; however, it is not as rigid as a stick. Typically, it is understood that gels are soft, deformable products while sticks are free-standing solids. For example, by Theological analysis, a commercial deodorant stick has been determined to have a plateau storage modulus G'(ω) of roughly at least 10$^5$ Pa and a complex viscosity of at least 10$^6$ Pa second (both at an angular frequency of 0.1 rad-sec). On the other hand, a commercial antiperspirant gel or cream may have a G'(ω) value of roughly about 10$^2$–10$^5$ Pa and a complex viscosity in the range of about 10$^3$–10$^6$ Pa second (at 0.1 rad-sec).

Cosmetic compositions according to the present invention include both a thickening agent and a solvent for the polyamide gelling agent (in the present application, the polyamide gelling agent and solvent for the gelling agent provide a vehicle for the active cosmetic material, and have been so designated as a vehicle).

Base and cosmetic compositions according to the present invention can easily be manufactured by methods known to those skilled in the art such as by using known mixing procedures. Base compositions according to the present invention can be made by mixing the various components at an elevated temperature (that is, by heating and mixing the various components) and then cooling in order to form the gelled (solidified) stick composition. For cosmetic compositions, the additional ingredients are added using techniques and at times in the manufacturing process as are known to those in the art. Desirably, any volatile components (such as fragrances) are added to the mixture at a relatively late stage of the mixing, so as to limit volatilization of the volatile components.

Generally, the solvent and thickening agent (for example, the polyamide gelling agent) are mixed and heated so as to fully dissolve the thickening agent in the solvent. An active ingredient (for example, antiperspirant active material, for example, in dry form or as part of a solution) can be added after the thickening agent fully dissolves, and mixing then takes place. Mixing continues with cooling, with, for example, colorant and fragrance then being added. Thereafter, the resulting composition, still liquid, is poured into canisters, for example, dispensing packages, and solidified, as with conventional stick compositions (for example, at room temperature or lower).

An illustrative and non-limiting example of the present invention is as follows. The silicone-based polyamide polymer can be dissolved in a mixture of the silicone fluid and organic component(s), for example, at elevated temperatures (for example, up to 120 degrees C.) so as to form a solution, with cooling then being performed to form the gel. It is preferred that the solution is not heated too long or at too high a temperature, since such disadvantageously may cause the gel to be colored (rather than colorless). The cosmetic active can be added to the solution of silicone fluid and polymer gelling agent and mixed therewith so as to be homogeneously distributed in the product.

For example, mixtures of the silicone fluids, organic emollients, and siloxane-containing polymers can be mixed at elevated temperatures so as to dissolve the polymer in the fluid mixture, with cosmetically active ingredients being added to the mixture of fluids and polymer. Upon cooling the mixture, the polymer forms a gel from the mixture, achieving the desired product. In the case where an aqueous phase is included, an emulsion stick is the result. The base compositions of the present invention are thermally reversible gels; that is, they form gels upon being cooled and are liquefied when heated. Where the product is a stick product, the molten product, at elevated temperatures, can be poured into dispensing containers and allowed to cool and harden therein.

While compositions according to the invention may be formed into sticks, creams, soft solids or more liquid products suitable for roll-ons (such liquid products having a viscosity not exceeding 2,000 centistokes), one of the important advantages of the invention is the ability to form products that require some structural integrity, especially sticks. In a series of preferred embodiments base compositions and cosmetic compositions according to the present invention contain a sufficient amount of the thickening agent such that the final cosmetic composition is a solid stick composition.

When a cosmetic composition according to the present invention is in the form of a stick product, the composition can be applied by elevating the stick out of the package so as to expose the end of the stick, and then rubbing the end of the stick on the skin in order to deposit stick material (including the cosmetically active material such as the antiperspirant active) on the skin. Thus, in the case of an antiperspirant, the active material on the skin is available to reduce body malodor and/or reduce the flow of perspiration from, for example, the axillary regions of the body.

In the following, illustrative examples of compositions within the scope of the present invention are set forth. These examples are illustrative of the present invention, and are not limiting. Amounts of components in these examples are in weight percent, of the total weight of the composition.

The cosmetic composition according to the present invention can be packaged in conventional containers, using conventional techniques. For example, where the composition is a stick composition, the composition, while still in liquid form, can be introduced into a dispensing package as conventionally done in the art, and cooled therein so as to thicken in the package. Thereafter, the product can be dispensed from the dispensing package as conventionally done in the art, to deposit the active material, for example, on the skin. This provides good deposition of the active material on the skin.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

Throughout the specification and claims all percents are in percents by weight unless stated otherwise. If no standard is indicated, then the percent by weight is in reference the total weight of the cosmetic composition.

A desired feature of the present invention is that a clear, or transparent, stick cosmetic composition, (for example, a clear or transparent deodorant or antiperspirant composition) can be provided. The term clear or transparent according to the present invention is intended to connote its usual dictionary definition; thus, a clear, for example, stick or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectro-photometer. As to this definition of clear, see European Patent Application Publication No. 291,334 A2. Thus, according to the present invention, there are differences between transparent (clear), translucent and opaque compositions.

Products of varying clarity and transparency can be formed. Clear cosmetic compositions can be formed if all the components of the particular cosmetic composition are soluble in each other, resulting in a single phase product. Clear cosmetic compositions can also be prepared from multiple phase compositions, for example, an emulsion or suspension, if each phase individually is clear and the refractive index of each phase is matched. Additionally, clear cosmetic compositions can be made from multiple phase compositions if the droplet (particle) size of the internal phase(s) are small enough, less than 0.2 micron. Examples of this are microemulsions and very fine particles in suspension. If the aforementioned conditions are not met, the cosmetic compositions will exhibit various degrees of transparency and opacity.

In the following, specific synthesis examples for forming siloxane-based polyamides of this invention are set forth, and specific examples of antiperspirant and deodorant compositions within the scope of the present invention are also set forth. These specific synthesis examples and examples are illustrative in connection with the present invention, and are not limiting. In the following, as well as throughout the present disclosure, names utilized are the CTFA (Cosmetics, Toiletry and Fragrance Association, Inc.) names, as set forth in the *CTFA International Cosmetic Ingredient Dictionary* (4th Ed. 1991), the contents of which dictionary are incorporated herein by reference in their entirety. Throughout the description of this invention chemical abbreviations and symbols have their usual and customary meanings, temperatures are in degrees C, all percents are in weight percents based on the total weight of the composition, and comprising shall be interpreted as including as subgroups consisting of and consisting essentially of. While particular siloxane-based polyamides are disclosed or used in the following Examples, it is to be understood that other siloxane-based polyamides meeting the criteria of the invention may also be substituted for the particular siliconized polyamide used in the examples and such compositions are within the spirit and scope of the invention.

EXAMPLES

Example 1

An antiperspirant/deodorant stick composition is formed by combining two phases. Phase A is made by combining 14% dioctyl ether (Cetiol OE from Henkel, Ambler, Pa.); 5% octyl salicylate (Escalol 587 from ISP, Bound Brook, N.J.), 20% phenyl trimethicone (Dow Coring 556 Fluid from Dow Corning Corporation, Midland, Mich.), and 13% of a polyamide as described in U.S. Pat. No. 5,981,680 with a DP=15 and a molecular weight "$M_w$" greater than 50,000. The mixture is heated to a temperature of 90 degrees C. with mild agitation until the mixture becomes clear. This mixture is cooled to a temperature of 75 degrees C. and 9% of a cyclopentasiloxane (Dow Coming 245 Fluid) is added with stirring. Phase B is made in a separate vessel by combining 4.7% propylene glycol, 32.3% of an active (30% Al/Zr tetrachlorohydrex glycine in propylene glycol), and a surfactant (Tween from ICI Surfactants, Wilmington, Del.) with mixing and heating to a temperature of 75 degrees C. Phase B is slowly added to Phase A with vigorous agitation and mixing is maintained for 10 minutes. The total mixture is then cooled to a temperature of 65 degrees C. Fragrance is added at a level of about 1% and mixing is continued for another 5 minutes. The total mixture is then poured into approximately 45 gram cosmetic product containers which are oval in cross-section and about 10 cm tall.

Example 2

The method described in Example 1 is repeated except that the types and amounts of ingredients listed below are used:
Phase A: 11% dioctyl ether; 12% isoparaffin (Isopar-H from Exxon, Baytown, Tex.): 16% phenyltrimethicone; 9% cyclopentasiloxane; 13% siliconized polyamide; and 1% fragrance.
Phase B: 29.2% of the antiperspirant active described in Example 1; 8% water; 0.8% cocamidopropyl hydroxysultane (Crosultaine C-50 from Croda, Inc., Parsippany, N.J.).

Example 3

The method described in Example 1 is repeated except that the types and amounts of ingredients listed below are used:
Phase A: 21% of the isoparaffin (Isopar-L from Exxon); 11% phenyltrimethicone; 12% cyclopentasiloxane; 13% siliconized polyamide; 4% isostearyl benzoate (Finsolv SB from Finetex, Inc., Elmwood Park, N.J.).
Phase B: 29% of the antiperspirant active described in Example 1; 9% water.

Example 4

The method described in Example 1 is repeated except that the types and amounts of ingredients listed below are used:
Phase A: 5% PPG-3 myristyl ether; 2% C12–C15 alkyl benzoate (Finsolv TN from Finetex); 5% octyl salicylate (Escalol 587 from ISP); 7.5% octylmethoxycinnamate (Escalol 557 from ISP); 8.2% phenyltrimethicone; 13.3% cyclopentasiloxane; 18% siliconized polyamide; and 1% fragrance.
Phase B: 5% propylene carbonate; 34% of the antiperspirant active described in Example 1; 1% Tween 20.

Example 5

The method described in Example 1 is repeated except that the types and amounts of ingredients listed below are used:
Phase A: 6% PPG-3 myristyl ether (Witconol APM from Witco, Dublin, Ohio); 1.5% dialkoxy-polydimethylsiloxane (Abil wax 2440 from Goldschmidt, Hopewell, Va.); 1.5% isostearyl alcohol; 5.8% phenyltrimethicone; 26.2% cyclopentasiloxane; 18% siliconized polyamide; 1% fragrance.
Phase B: 19% water; 19% Al/Zr tetrachlorohydrex glycine (Rezal 36GP from Reheis, Berkeley Heights, N.J.); 1% Polysorbate-20 (Tween 20; ICI Surfactants, Wilmington, Del.); 1% cocamidopropyl hydroxysultaine.

Example 6

The method described in Example 1 is repeated except that the types and amounts of ingredients listed below are used:
Phase A: 17% isoparaffin (Isopar-H from Exxon); 4.5% phenyltrimethicone; 19.5% cyclopentasiloxane; 18% siliconized polyamide; and 1% fragrance.
Phase B: 19% water; 19% of the antiperspirant active described in Example 1; 2% cocamidopropyl hydroxysultaine.

Example 7

Clear Gel

The method described in Example 1 for making a clear stick ma be modified to make a clear gel. The non-volatile components in Phase A (PPG-3 myristyl ether, octyl dodecyl benzoate, siliconized polyamide and phenyltrimethicone) are heated to a temperature of 90 degrees C. with mild agitation until the gellant melts. The mixture is cooled to 75 degrees C. and cyclomethicone (preheated to 70 degree C.)

is added with stirring. Phase B is made in a separate vessel with mixing and heating to a temperature of 75 degrees C. Phase B is slowly added to Phase A with vigorous agitation and mixing is maintained for 5 minutes. The fragrance is added at a temperature of 70 degrees C. and mixture is poured at a temperature of 65 degree C. into suitable cosmetic product containers, for example the oval type barrels having dimensions along the main axis of 5 cm×2.5 cm×8.7 cm.

Phase A: 10% PPG-3 myristyl ether (Witconol APM from Witco, Dublin, Ohio); 4% octyl dodecyl benzoate (Finsolv BOD from Finetex, Inc., Elmwood Park, N.J.); 2% siliconized polyamide; 5% phenyltrimethicone; 18% cyclomethicone; 1% fragrance;

Phase B: 57% of the antiperspirant active described in Example 1; 2% water; 1% polysorbate 20.

Example 8

Soft Solid

A soft solid may be made by the following method. PPG-3 myristyl ether and siliconized polyamide gellant are mixed and heated to 90 degrees C. until the gellant melts. The mixture is cooled to a temperature of 75 degrees C. In a separate container, the cyclomethicone described in Example 1 for Phase A is mixed with an antiperspirant active powder as described in Example 1 for Phase B and the mixture is heated to 75 degrees C. The mixture from the second container is slowly added to the mixture in the first container with stirring. Next the fragrance is added and the entire mixture is mixed vigorously for 5 minutes. The stirred mixture is then poured at a temperature of 70 degrees C. into appropriate cosmetic containers such as the one described in Example 7, but with a top having slots therein or formed with a screen type porous structure and holding about 4.5 grams of product.

Phase A: 20% PPG-3 myristyl ether (Witconol APM); 46.75% cyclomethicone; 7% siliconized polyamide; 1.25% fragrance;

Phase B: 25% antiperspirant active powder (for example, AZP 902 from Reheis, Berkeley Heights, N.J.)

Comparative Examples

An important feature of the invention is the reduced crumbling of the cosmetic sticks made according to this invention. The following data describes test results which demonstrate the reduced crumbing of sticks that is obtained when using this invention.

A series of sticks were made using the process of Example 2 for the sticks that used a polyamide with a DP of 15 and using the process of Example 2 for the sticks that used a polyamide with a degree of polymerization of 30. The amount of polyamide was varied as listed in TABLE B. For gellant levels less than 30%, additional cyclomethicone was added to make up the difference. The failure under stress was measured for each of the sticks using the three point bend test described above. The data is described in TABLE A and the results show the superiority of the polyamide having a DP=15.

TABLE B

| Gellant level and DP | Failure Stress (Pascal units) as Results of 3-Point Bending Test |
|---|---|
| 15%/DP = 15 | 11.9 |
| 23%/DP = 15 | 25.6 |
| 30%/DP = 15 | 40.1 |
| 15%/DP = 30 | 9.7 |
| 23%/DP = 30 | 17.5 |
| 30%/DP = 30 | 28.1 |

Evaluation of Residue Level

A group of 6 people evaluated a product made according to Example 4 for residue. The product was applied to the forearm by applying 4 swipes to the forearm. The product was clear and did not leave any appreciable white residue.

We claim:

1. A clear stick antiperspirant and/or deodorant cosmetic emulsion composition having a failure stress of at least 2.0 Pascals comprising:

(a) at least 8% by weight based on the total weight of the composition of at least one siliconized polyamide of Formula IIIA:

Formula IIIA

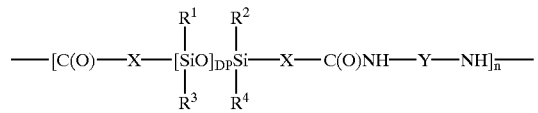

where:

(1) DP is a number in the range of 12–18;
(2) n is a number selected from the group consisting of 40–100;
(3) X is a linear or branched chain alkylene having 3–10 carbons;
(4) Y is selected from the group consisting of linear and branched chain alkylenes having 2–6 carbons, wherein:
 (A) the alkylene group may optionally and additionally contain in the alkylene portion at least one of the members of a group consisting of (i) 1–3 amide linkages; (ii) C5 or C6 cycloalkane (as a cycloalkylene linkage); and (iii) phenylene optionally substituted by 1–3 members selected independently from the group consisting of C1–C3 alkyls; and
 (B) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1- C6 alkyl amine;

or Y=$Z^2$ where

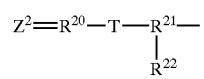

wherein each of $R^{20}$, $R^{21}$ are independently selected from the group consisting of linear and branched C1–C10 alkylenes; $R^{22}$ is selected from the group consisting of linear and branched C1–C10 alkanes;

and T is selected from the group consisting of (i) a trivalent atom selected from N, P and Al; and (ii) —CR, where R is selected from the group consisting of hydrogen, methyl, ethyl, propyl, isopropyl, a siloxane chain, and phenyl, wherein the phenyl may optionally be substituted by 1–3 members from the group consisting of methyl and ethyl; and (5) each of $R^1$–$R^4$ is independently selected from the group consisting of methyl and ethyl;

wherein the polyamide of Formula IIIA has:
(i) a silicone portion in the acid side of the polyamide;
(ii) an average molecular weight of at least 50,000 daltons with at least 95% of the polyamide having a molecular weight greater than 10,000 daltons; and
(iii) a polydispersity of less than 20;

(b) 15–25% of a silicone fluid;
(c) 5–50% of a non-silicone organic emollient selected from the group consisting of isocetyl alcohol, isostearyl alcohol; isopropyl palmitate, isopropyl isostearate, octyl stearate, hexyl laurate, isostearyl lactate; petroleum distillates, light mineral oils, guerbet alcohols; organic esters having 14–22 carbons; hydrocarbons which are liquids at ambient temperature and mixtures of any of the foregoing, and added in an amount so that the ratio of non-silicone organic emollient to silicone fluid (including organosilicones) is in the range of 10:1–0.01:1;
(d) an internal phase which internal phase comprises:
(i) at least one non-ethanol based antiperspirant active; and
(ii) one or more members selected from the group consisting of water; a glycol component; polyhydric alcohols having 3–9 carbons; branched and unbranched polymeric ethers having 6–18 carbons and 5–30 ethylene oxide groups;
dibenzylidene sorbitol; polyvinyl alcohol; polyvinylpyrrolidone; and mixtures of the foregoing; and
(iii) a water content below 25% by weight based on the weight of the entire composition.

2. A composition as claimed in claim 1 wherein the siliconized polyamide is added in an amount of 8–18%.

3. A composition as claimed in claim 1 wherein the siliconized polyamide has a polydispersity of less than 10.

4. A composition as claimed in claim 1 wherein the siliconized polyamide has a polydispersity of less than 4.

5. A composition as claimed in claim 5 wherein the DP is 15.

6. A composition as claimed in claim 1 wherein $R^1$–$R^4$ are each methyl.

7. A composition as claimed in claim 1 wherein the siliconized polyamide is a polyamide of Formula IIIB:

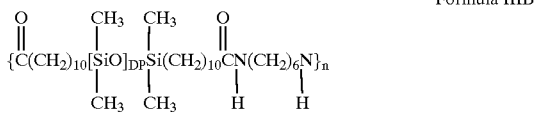

Formula IIIB where DP is from 12–18 and n is selected to give an average molecular weight of at least 50,000 daltons.

8. A composition as claimed in claim 1 wherein the DP=15.

9. A composition as claimed in claim 8 wherein for the siliconized polyamide of Formula IIIB, the DP is 15.

10. A composition as claimed in claim 1 wherein for the siliconized polyamide of Formula IIIA, X, Y, DP and $R^1$–$R^4$ remain the same in each polymeric unit.

11. A composition as claimed in claim 7 wherein for the siliconized polyamide of Formula IIIB, DP and n remain the same for each polymeric unit.

12. A composition as claimed in claim 1 wherein for the siliconized polyamide of Formula IIIA, the polyamide contains multiple siloxane block lengths of Formula IIIC:

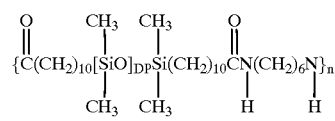

Formula IIIB where X, Y, n, and $R^1$–$R^4$ have the meanings described for Formula IIIA; m is selected from the same group as n, and n and m denote the total number of units enclosed within the brackets in a regular, alternating, block or random sequencing; $R^5$–$R^8$ is selected from the same group as defined for $R^1$–$R^4$; DP1 and DP2 may be the same or different and are each independently selected from the same group as defined for DP; and the units denominated by n and m may be structured to form either block or random copolymers.

13. A composition as claimed in claim 12 wherein for the polyamide block lengths of Formula IIIC, all of the R groups are methyl.

14. A composition as claimed in claim 12 wherein for the siliconized polyamide having block lengths of Formula mc, DP1=DP2.

15. A composition as claimed in claim 12 wherein for the siliconized polyamide having block lengths of Formula IIIC, all of the R groups are selected to be methyl and DP1=DP2.

16. A composition as claimed in claim 1 wherein the average molecular weight of the siliconized polyamide is at least 70,000 daltons.

17. A composition as claimed in claim 1 comprising two or more gellants which together total 10–90% of the composition.

18. A composition as claimed in claim 1 further comprising at least one additional ingredient selected from the group consisting of silicone gums, elastomers, polymethylmethacrylate, polyethylene, polypropylene, polytetrafluoroethylene, silicone resins of an MQ type, and inorganic particulates selected from the group consisting of silicas, talcs, clays and silicates.

19. A composition as claimed in claim 18 wherein the MQ resin is a member selected from the group represented by Formula IIA:

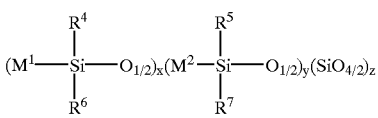

Formula IIA wherein
$R^4$, $R^5$, $R^6$, and $R^7$ are each independently selected from the group consisting of phenyl and C1–C12 branched and unbranched hydrocarbons;
$M^1$ and $M^2$ are each independently from the group consisting of
(a) hydrogen,
(b) phenyl, (c) phenethyl,
(d) a polyether of Formula IIB:

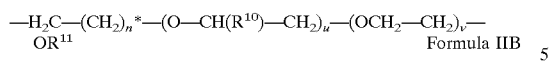

Formula IIB where n* is a number from 1–20 and the —(CH$_2$)— chain may optionally contain 1 or 2 unsaturations; u and v are integers each independently selected from 0–20, provided that u+v≧1; R$^{10}$ is selected from C1–C20 alkyl; and R$^{11}$ is selected from the group consisting of H, —CH$_3$ and —C(O)CH$_3$); and (e) C1–C24 branched and unbranched hydrocarbons optionally substituted by a halogen substituted C1–C3 hydrocarbon radical;

wherein (x+y)/z is a number in the range of 0.5 and 1.5; and the values for R$^4$, R$^5$, R$^6$, R$^7$, x, y, z, M$^1$ and M$^2$ are selected so that the MQ resin is a liquid having a viscosity of $1.0 \times 10^3 - 1 \times 10^6$ centipoise.

20. A composition as claimed in claim 1 comprising 5–20% on an anhydrous basis of an antiperspirant active.

21. A composition according to any one of claims 1–20 wherein the polyamides have a molecular weight in the range of 80,000–150,000 daltons.

22. A composition according to any one of claims 1–20 wherein the polyamides have a molecular weight in the range of 90,000–120,000 daltons.

* * * * *